US00PP34550P2

(12) United States Plant Patent
Van Swieten

(10) Patent No.: US PP34,550 P2
(45) Date of Patent: Sep. 6, 2022

(54) ***PHALAENOPSIS* ORCHID PLANT NAMED 'PHA329719'**

(50) Latin Name: ***Phalaenopsis* hybrid**
Varietal Denomination: PHA329719

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,307

(22) Filed: Apr. 28, 2022

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHA329719', particularly characterized by having reddish-purple flowers with light purple edges and reddish-purple lips, flowers that are flat in lateral view, dorsal sepals with incurving curvature of the longitudinal axis, and is propagated by meristem tissue culture, is disclosed.

3 Drawing Sheets

Genus and species: *Phalaenopsis* hybrid.
Variety denomination: 'PHA329719'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA329719'.

The new *Phalaenopsis* plant is a product of a planned breeding program conducted by the inventor in Bleiswijk, the Netherlands. The objective of this breeding program was to create a new *Phalaenopsis* plant with numerous attractive reddish-purple flowers with light purple edges and reddish-purple lips, suitable for potted plant production.

The new *Phalaenopsis* plant 'PHA329719' is a result of cross-pollination made by the inventor in February 2013 in Bleiswijk, the Netherlands, of the proprietary female, or seed parent, *Phalaenopsis* hybrid 'PHALUFREL' (U.S. Plant Pat. No. 29,259) with the proprietary male, or pollen parent, *Phalaenopsis* hybrid '47474-02' (unpatented).

The new *Phalaenopsis* was selected by the inventor as a single plant within the progeny of the stated cross-pollination in a controlled greenhouse in Bleiswijk, the Netherlands, in January 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1115), by Applicant who obtained the subject matter disclosed directly from the inventor. 'PHA329719' has not been made publicly available or sold anywhere in the world prior to the effective filing date of this application with the exception of sales or disclosures made one year or less before the effective filing date of this claimed invention by Applicant who obtained 'PHA329719' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA329719' as a new and distinct variety of *Phalaenopsis* plant:

1) Reddish-purple flowers with light purple edges and reddish-purple lips;
2) Flower shape in lateral view is flat; and
3) Curvature of the longitudinal axis of the dorsal sepal is incurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in March 2022. Colors in the photographs may differ from the color values cited in the detailed botanical description, which accurately describe the actual colors of the new variety.

DESCRIPTION OF THE NEW VARIETY

Figure 1:
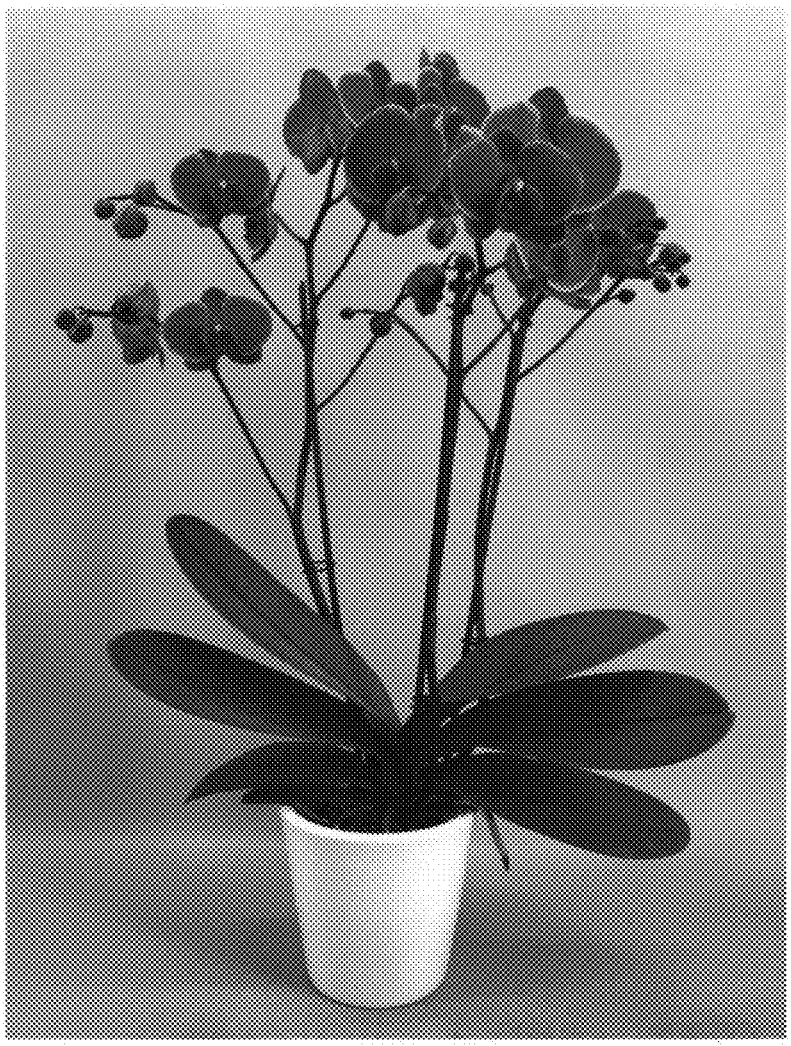
FIG. 1 shows the overall plant habit, including blooms, buds, and foliage of 'PHA329719'.
Figure 2:
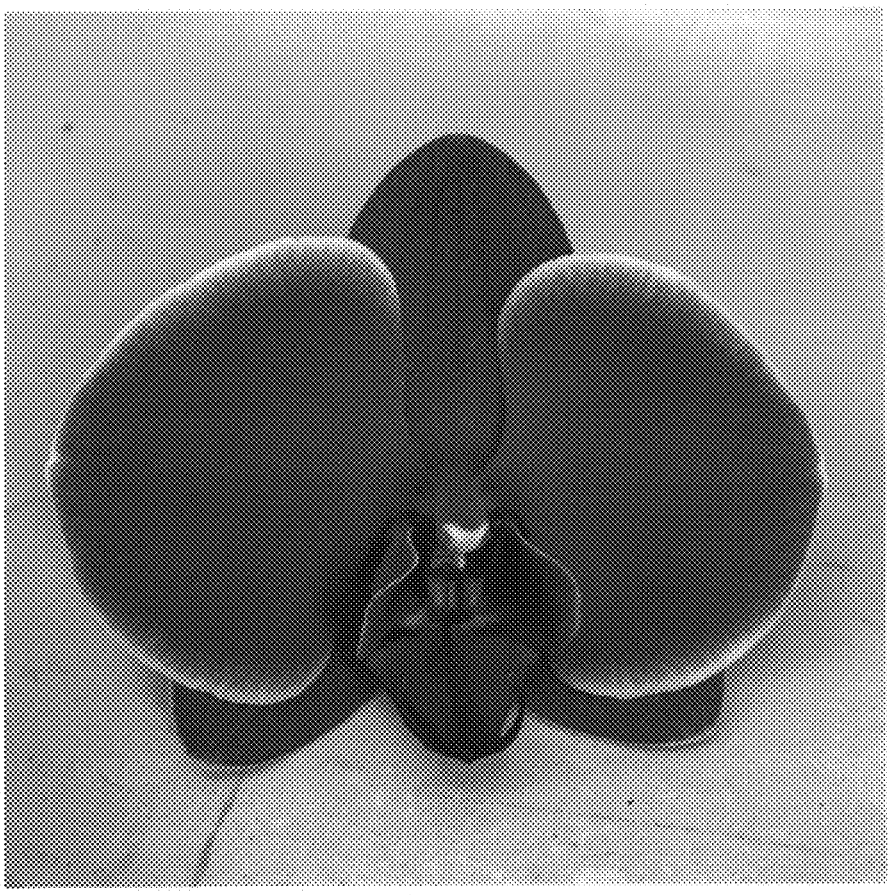
FIG. 2 shows a close-up of a flower of 'PHA329719'.
Figure 3:
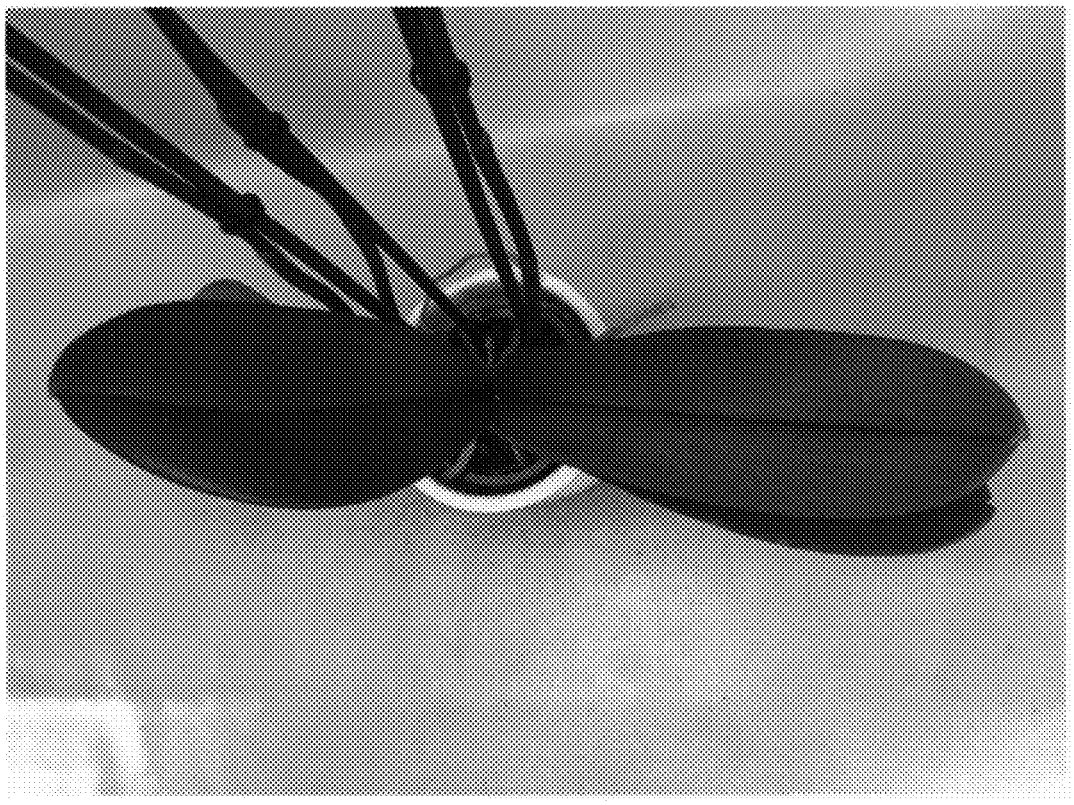
FIG. 3 shows an overhead view of the leaves of 'PHA329719'.

The following detailed description sets forth the distinctive characteristics of 'PHA329719'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA329719'.

Parentage:

*Female parent*.—*Phalaenopsis* cultivar 'PHALUFREL' (U.S. Plant Pat. No. 29,259).

*Male parent*.—*Phalaenopsis* cultivar '47474-02' (unpatented).

Propagation:

*Type*.—Meristem tissue culture.

Roots:

*Root description*.—Greyed-green (a color in between RHS 190B and RHS 190C) colored roots with branching lateral roots having reddish-purple (RHS N78B) with a touch of greenish-yellow (RHS 4C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 56.0 cm to 61.0 cm.

*Width* (*measured from leaf tips*).—About 43.0 cm to 48.0 cm.

*Vigor*.—Strong.

Leaves:

*Mature leaves*.—Quantity per plant: 7 to 8 leaves are produced before flowering. Length (fully expanded): 22.0 cm to 24.0 cm. Width: 7.0 cm to 8.0 cm. Position of the broadest part of the leaf: At the middle. Shape: Oblong. Base shape: Moderately elongated to very elongated. Apex: Obtuse asymmetric. Leaf blade angle with the petiole (measured from the horizontal position): Between 25 degrees and 40 degrees. Leaf margin: Entire. Color: Upper surface: RHS 146A with a dark red margin (RHS 187B) toward the tip. Lower surface: RHS 146B with a purple margin and shade (RHS N77A) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a hint of dark purplish-red (RHS N79B).

Peduncle:

*Quantity per plant*.—1 to 3.

*Number of flowers per peduncle*.—15 to 22.

*Length*.—56.0 cm to 61.0 cm.

*Diameter*.—6.0 mm to 7.0 mm.

*Strength*.—Strong.

*Aspect*.—Upright to slightly pendent.

*Texture*.—Smooth.

*Color*.—Mix of brown (RHS 200A) and yellow-green (RHS 146D).

*Internode length*.—3.0 cm to 4.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 3.

*Inflorescence size*.—Height (from base to tip): 250.0 mm to 350.0 mm.

*Flowering time*.—First flowers can be expected 10 to 11 months after planting in a 12-cm pot.

*Flower*.—Height: 68.0 mm to 73.0 mm. Diameter: 78.0 mm to 83.0 mm. Depth of lip: 22.0 mm to 24.0 mm.

*Flower shape*.—Flat.

*Flower longevity*.—On the plant: 11 to 13 weeks.

*Fragrance*.—Absent.

*Flower bud*.—Average size: Large. Length: 20.0 mm to 22.0 mm. Width: 19.0 mm to 21.0 mm. Shape: Egg shaped. Color: Touch of yellow-green (RHS 146D) at the base; purplish-red (RHS N77B) with a dark purple-red shade (RHS N79C) and dark purplish-red stripes (RHS N79B).

*Petals*.—Arrangement: Open/free. Shape: Semi-circular. Apex: Emarginated asymmetric. Margin: Entire. Length (from base to tip): 37.0 mm to 39.0 mm. Width: 48.0 mm to 50.0 mm. Position of the broadest part of the petal: Toward the base. Color (when fully opened): Upper surface: Basic color: Reddish-purple (RHS N78A). Over color: Light purple dots (RHS 76A) toward base; dark reddish-purple stripes (a color in between RHS N79C and RHS N78A) toward the tip and light purple edge (RHS 76A). Lower surface: Basic color: Reddish-purple (RHS N78B). Over color: Touch of white (RHS NN155C) at the base and light reddish-purple (RHS N78D) at base toward the middle and very light purple margin (RHS 76B). Number of spots, dots, and stripes on the petals (upper surface): Few to medium small dots and many stripes. Color of spots, dots, and stripes on the petals (upper surface): Dots (RHS 76A) and stripes (a color in between RHS N79C and RHS N78A). Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 39.0 mm to 41.0 mm. Width: 28.0 mm to 30.0 mm. Position of the broadest part of the dorsal sepals: At the middle. Color (when fully opened): Upper surface: Basic color: Reddish-purple (RHS N78A). Over color: Dark purplish-red shade and stripes (RHS N79C) and very small light reddish-purple dots (RHS N78D). Lower surface: Basic color: Reddish-purple (RHS N78B). Over color: Yellowish-green (RHS 195B) at the middle from the base toward the tip and stripes (a color in between RHS N79C and RHS N79D). Number of spots, dots, and stripes on the dorsal sepals (upper surface): Many of very small dots and medium stripes. Color of spots, dots, and stripes on the dorsal sepals (upper surface): Dots (RHS N78D) and stripes (RHS N79C). Density of netting of the dorsal sepals (upper surface): Low. Color of the netting: RHS N79C.

*Lateral sepals*.—Shape: Ovate. Apex: Obtuse asymmetric. Margin: Entire. Length (from base to tip): 40.0 mm to 42.0 mm. Width: 25.0 mm to 27.0 mm. Position of the broadest part of the lateral sepals: Toward the base. Color (when fully opened): Upper surface: Basic color: Reddish-purple (RHS N78A). Over color: Touch of light yellow-green (RHS 145D) at the base; dark purplish-red stripes and netting (RHS N79C) and light reddish-purple dots (RHS N78D). Lower surface: Basic color: Purplish-pink (RHS N78C). Over color: Light yellow-green (RHS 145C) and stripes (a color in between RHS N79C and RHS N79D). Number of spots, dots, and stripes on the lateral sepals (upper surface): Many of very small dots at the base and medium stripes. Color of spots, dots, and stripes on the lateral sepals (upper surface): Dots (RHS N78D) and stripes (RHS N79C). Density of netting of the lateral sepals (upper surface): Low. Color of the netting (upper surface): RHS N79C.

*Labellum* (*lip*).—Whiskers: Present. Length of whiskers: 13.0 mm to 15.0 mm. Color of whiskers: Dark purplish-red (a color in between RHS N79B and RHS N79C) on one side and dark red (RHS 187A) on the other side; yellowish-white (RHS 155B) toward the tip. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 19.0 mm to 21.0 mm. Width: 14.0 mm to 16.0 mm. Color: Upper surface: Touch of white (RHS N155B) at the base and light yellow (RHS 8D) on one margin; reddish-purple (RHS N78A) with dark red stripes and shade (RHS 59A) at the base; white margin (RHS NN155C) toward the tip. Lower surface: White (RHS 156D) at the base with a touch of light yellow (RHS 8D) toward margins; light reddish-purple (RHS N78D) and reddish-purple (RHS N78A) toward the tip; dark red margin (RHS 187C) on one side. Number of spots and stripes on the lateral lobe: Few stripes. Color of spots and stripes on the lateral lobe: RHS 59A. Density of netting of the lateral lobe: None. Color of the netting: None.

*Apical lobe*.—Shape: Triangular. Margin: Entire. Length: 18.0 mm to 20.0 mm. Width: 20.0 mm to 22.0 mm. Color: Upper surface: Reddish-orange margin (RHS 175D) at the base; dark purplish-red (RHS N79C) with a touch of dark red shade (RHS 187C) at the base and dark red midvein (RHS 187B). Lower surface: Dark red margin (RHS 183B) at the base toward margin with a touch of reddish-orange (RHS 174D); yellow-green (RHS 196C) at the middle from base toward whiskers; reddish-purple (RHS N78A) toward margins on sides. Number of spots and stripes on the apical lobe: None. Color of spots and stripes on the apical lobe: None. Density of netting of the apical lobe: None. Color of the netting: None. Bump and ridge: Absent.

*Callus*.—Average size: Medium to large. Height: 7.0 mm to 8.0 mm. Length: 6.0 mm to 7.0 mm. Width: 4.0 mm to 5.0 mm. Color: Yellow tips (RHS 12A); white (RHS N155C) on sides; flecked (RHS 183C).

Reproductive organs:

*Column*.—Length: 9.0 mm to 10.0 mm. Diameter: 5.0 mm to 6.0 mm. Color: Reddish-purple (RHS N78A).

*Pollinia*.—Quantity: 2. Diameter: 0.9 mm to 1.0 mm. Color: Orange (RHS 23A).

*Ovary*.—Length: 14.0 mm to 16.0 mm. Diameter: 2.0 mm to 2.5 mm.

*Pedicel*.—Length: 36.0 mm to 40.0 mm. Diameter: 2.6 mm to 3.0 mm. Color: Yellow-green (RHS 146A) at the base; light yellow-green (RHS 145C) with a touch of light reddish-purple (RHS N78D) toward the flower Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA329719' differs from the female parent plant 'PHALUFREL' (U.S. Plant Pat. No. 29,259) in that 'PHA329719' has flowers with a medium edge pattern, whereas 'PHALUFREL' has flowers with a broad edge pattern. Additionally, 'PHA329719' has smaller flowers and longer whiskers than 'PHALUFREL'

The male parent plant of 'PHA329719', cultivar '47474-02' (unpatented), is no longer in existence, therefore a meaningful comparison cannot be made.

'PHA329719' is most similar to the commercial *Phalaenopsis* plants named 'PHALLINCG' (U.S. Plant Pat. No. 33,524) and 'PHALHITWOQ' (U.S. Plant Pat. No. 32,283). 'PHA329719' differs from the commercial variety 'PHALLINCG' in that 'PHA329719' has emarginated petal apexes, whereas 'PHALLINCG' has rounded petal apexes. Additionally, 'PHA329719' has smaller flowers and longer whiskers than 'PHALLINCG'.

'PHA329719' differs from the commercial variety 'PHALHITWOQ' in that 'PHA329719' has petals with weak undulation of the margin, whereas 'PHALHITWOQ' has petals with medium undulation of the margin. Additionally, 'PHA329719' has smaller flowers and longer whiskers than 'PHALHITWOQ'.

I claim:

1. A new and distinct variety of *Phalaenopsis* plant named 'PHA329719', substantially as described and illustrated herein.

* * * * *